United States Patent [19]

Landis

[11] Patent Number: 4,701,965

[45] Date of Patent: Oct. 27, 1987

[54] VISOR-TYPE MASK FOR DENTISTS

[76] Inventor: Timothy J. Landis, 1046 Mangrove Ave., Chico, Calif. 25926

[21] Appl. No.: 842,150

[22] Filed: Mar. 21, 1986

Related U.S. Application Data

[63] Continuation-in-part of Ser. No. 786,750, Oct. 11, 1985.

[51] Int. Cl.⁴ .......................... A61F 9/02; A41D 13/00
[52] U.S. Cl. ................................................. 2/428; 2/9; 128/139
[58] Field of Search ............. 2/9, 12, 427, 428; 128/139, 200.28

[56] References Cited

U.S. PATENT DOCUMENTS

| | | | |
|---|---|---|---|
| 797,293 | 8/1905 | Lang | 2/12 |
| 2,262,449 | 11/1941 | Buegeleisen | 2/9 |
| 2,665,686 | 1/1954 | Wood et al. | 2/9 |
| 2,818,859 | 1/1958 | Peterson | 2/9 |
| 3,152,588 | 10/1964 | Rogowiski | 2/9 |
| 4,475,254 | 10/1984 | Boy | 2/12 |

Primary Examiner—Doris L. Troutman
Attorney, Agent, or Firm—Julian Caplan

[57] ABSTRACT

A mask to protect dentists from handpiece splatter which contains all manner of germs and viruses and has a visor which attaches to the head above the eyes and a transparent shield which extends down below the mouth. The shield is preferably detachable from the visor for cleaning and replacement. The visor has a vent for air circulation which may be closed by a cover for protection. A filter may be applied to the shield for eye protection when ultraviolet light is being used for curing plastic tooth cavity fillings.

30 Claims, 16 Drawing Figures

VISOR-TYPE MASK FOR DENTISTS

CROSS-REFERENCE TO RELATED APPLICATION

This application is a continuation-in-part of co-pending application Ser. No. 786,750, filed Oct. 11, 1985 pending.

BACKGROUND OF THE INVENTION

1. Field of the Invention

This invention relates to a new and improved plastic mask for use by dentists, surgeons, and others who may be contaminated with germs and viruses of their patients and customers. The mask is supported by a band which fits across the forehead and around both sides of the head above the ears and comprises an upper or visor part which is integral with or attached to the band and a removable, disposable transparent shield which snaps onto the visor and extends substantially vertically down below the level of the mouth of the wearer. The shield protects the eyes, nose and mouth of the wearer, but does not interfere with normal breathing. The visor is provided with a vent which may be opened and closed as conditions require. Coated on or otherwise applied to the shield is a filter to protect the eyes from ultraviolet, blue or other harmful radiation from instruments which are presently used by dentists in curing tooth-filling plastic.

2. Description of Related Art

Surgical masks of gauze and paper have been used by surgeons and sometimes by dentists to prevent intercontamination of the doctor and patient. However, wearing such masks is hot and uncomfortable and, frequently, frightening to patients. Putting the masks on and removing them are time consuming and often difficult. Breath condenses within the mask and the latter becomes saturated with moisture and thereby fails to be an effective barrier to viruses and bacteria.

Surgical masks cause the wearer to re-inhale exhaled breath causing the $CO_2$ content of the blood to rise. The result of this may be increased heart and respiration rates and higher body temperatures and perspiration.

Safety face shields with vents, but of different construction include U.S. Pat. Nos. 3,152,588; 3,298,031; 3,678,929; and 4,250,477.

Detachable masks are shown in British Pat No. 503,750 and U.S. Pat. Nos. 1,279,884; 2,818,829; and 3,346,875. Mere face shields are shown in U.S. Pat. No. 2,978,709, for example.

Additionally, shields attached to eyeglass-type frames are shown in German Pat. No. 688,227; U.S. Pat. Nos. 1,582,164 and 2,774,970.

SUMMARY OF THE INVENTION

The present invention is in two pieces. The first piece has a band which is resilient and fits across the forehead and around the sides of the head above the ears, being sufficiently resilient so as to hold the mask in place. Projecting forwardly from the band is a visor which has an opening therein which may be closed by a cover which may be raised and lowered to control ventillation.

A removable, preferably disposable transparent flexible plastic shield is connected to the visor by snaps or other means. The shield is curved and downwardly tapered to protect the eyes, nose and mouth of the wearer from contamination. Between uses the shield may be cleaned or, if cost considerations are not too great, may be discarded to prevent cross-contamination of patients.

The shield protects the wearer from handpiece "splatter" and foreign objects such as filling and tooth structure and viruses. Burrs throw off saliva, tooth particles and the like. Similarly, high pressure water and air spread contaminants. These may enter the eye, nose and mouth of the dentist if not masked.

Since the shield is detachable, it may be removed between patients or whenever it becomes contaminated for cleaning or replacement.

There is provision in the mask for air circulation so that carbon dioxide build-up from re-breathing expelled air does not occur. Venting also prevents fogging the eye-glass lenses of the wearer if used. The vents are so located, however, that they do not defeat the anti-contamination features of the invention. Thus, the bottom of the shield is located forwardly of the mouth and nose, permitting air to flow up from below the face of the wearer into the space under the shield. Further, as has been mentioned, a vent is provided in the visor above the shield. Detritis from the mouth of the patient, however, cannot enter the vents because they are located out of a direct line of travel. If desired, a hinged or snap-in cover may be used to close off the vent in the visor. Other objects of the present invention will become aparent upon reading the following specification and referring to the accompanying drawing in which similar characters of reference represent corresponding parts in each of the several views.

Figure 2:
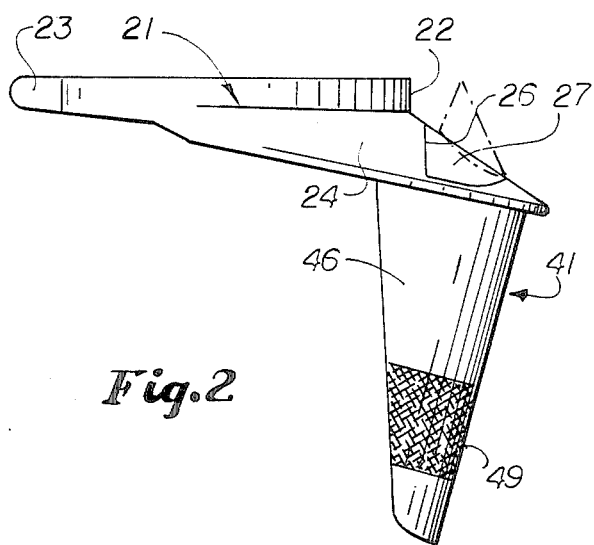
FIG. 2 is a side elevational view thereof.
Figure 3:
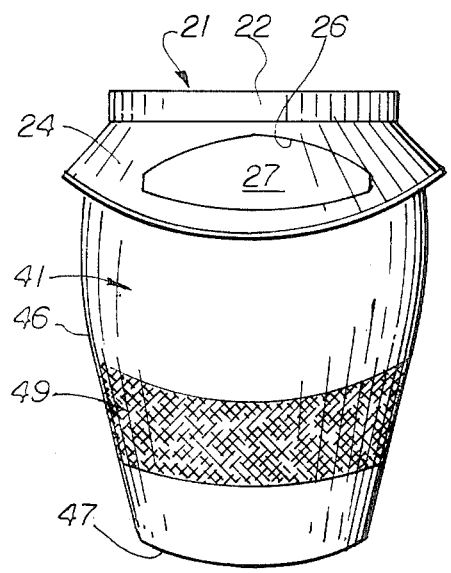
FIG. 3 is a front elevation.
Figure 4:
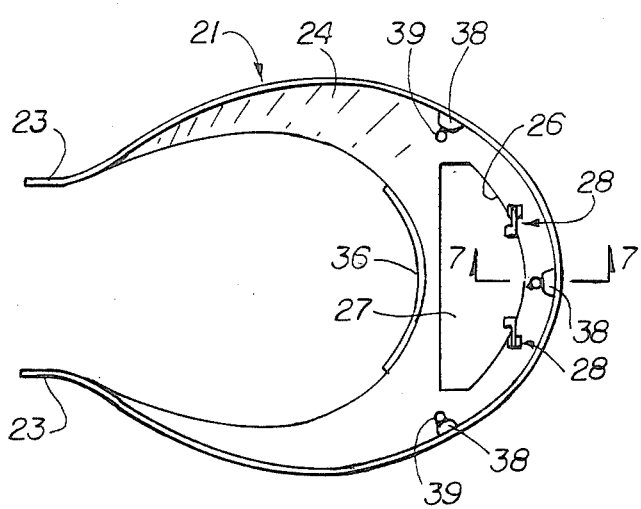
FIG. 4 is a bottom plan view.
Figure 5:
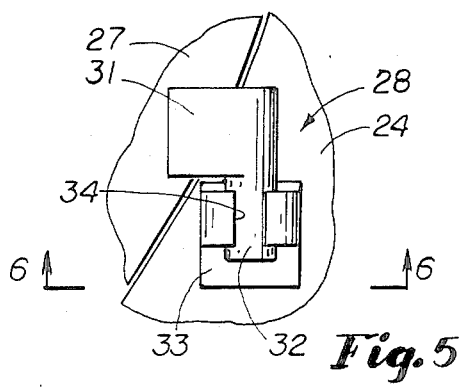
FIG. 5 is an enlarged fragmentary view showing the hinge of the closure for the vent.
Figure 6:
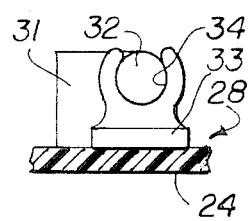
FIG. 6 is a fragmentary sectional view taken substantially along the lines 6—6 of FIG. 5.

The shield of the present invention is supported by means of a band 21 of a material such as polyethylene which is resiliently flexible. The center portion 22 fits around the forehead of the wearer and extends around the sides of the head terminating in ends 23 on either side which grip the head sufficiently strongly to hold the device in place without creating discomfort. Integral with and extending forwardly from the band 21, is a visor 24 shaped in the manner of a conventional sun visor. In the center of visor 24 is an opening 26 having a straight rear edge and a curved front edge which may be closed off by a cover 27. Cover 27 is connected to the visor 24 adjacent to front margin of the opening 26 by hinges 28. In the particular type of hinge illustrated herein, there is a leaf 31 fixed to the forward edge of cover 27, having outwardly extending hinge pins 32. Leaf 33 is fixed to visor 24 adjacent the opening 26 on either side of the device and is formed with a socket 34 into which the pin 32 snaps. By the pin 32 oscillating within the socket 34, the cover 27 may be raised from the solid line position of FIG. 2 to the dotted line position thereof. It will be understood that the details of construction of hinge 28 are subject to modification. In raised position, ventilation is achieved. Nevertheless, the fact that the cover 27 in open position slants upwardly-rearwardly prevents foreign objects from falling into the opening 26.

For comfort of the wearer, a resilient sponge-rubber pad 36 may be fixed to the inside of the band 21 to cushion contact of the latter with the skin of the wearer.

Fixed in the plurality of positions (here shown as three in number) on the lower edge of visor 24 are bosses 28 having studs 29 projecting therefrom.

Figure 8:
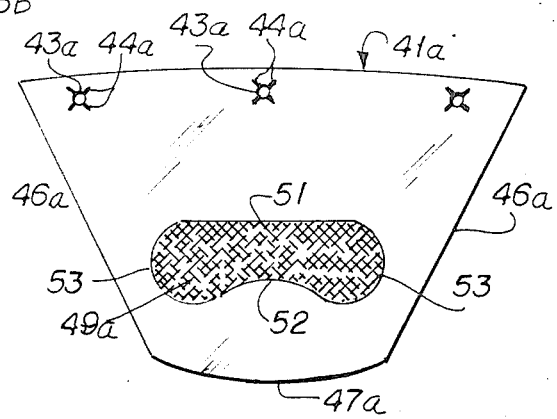
Figure 11:
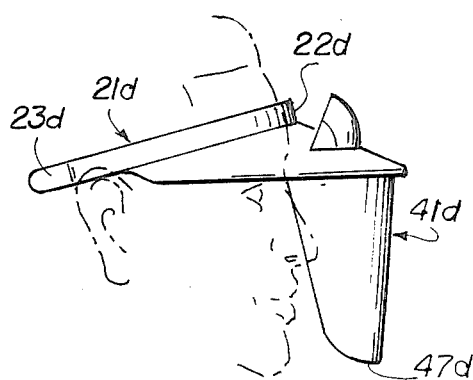
FIG. 11 is a view similar to FIG. 1 of a modification.
Figure 12:
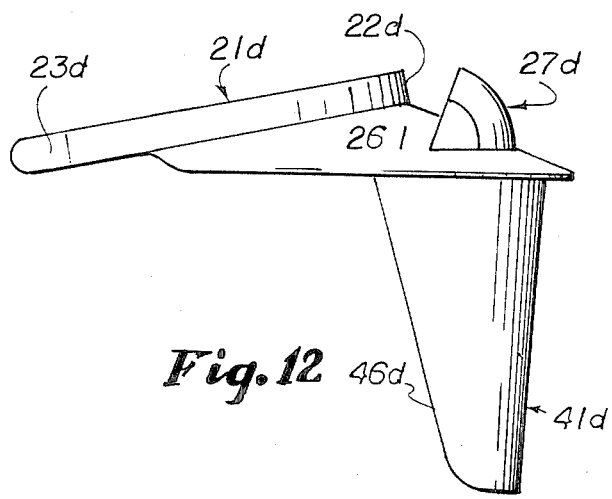
FIG. 12 is an enlarged side elevation of the mask of FIG. 11.
Figure 15:
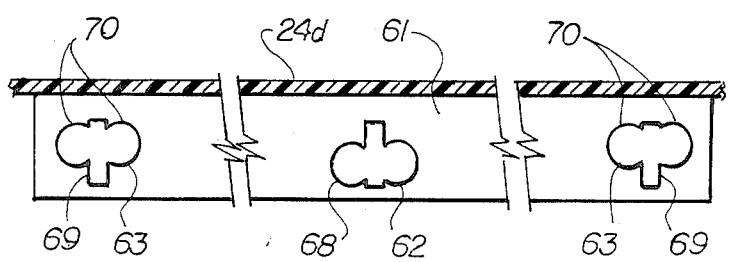
FIG. 15 is a fragmentary elevational view of a portion of FIG. 13 developed in a plane.
Figure 13:
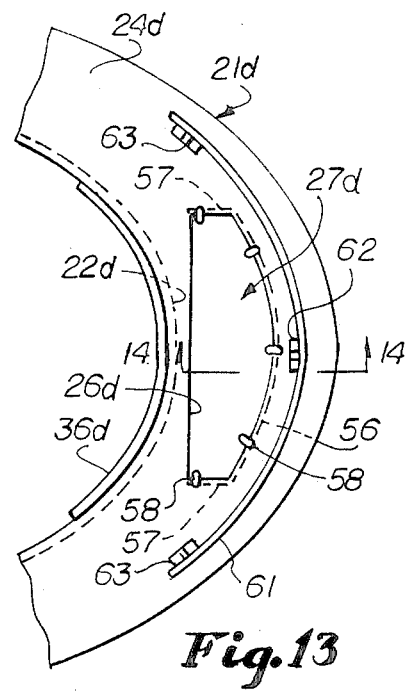
FIG. 13 is a bottom plan thereof.

A shield 41 (of which several varieties are illustrated and hereinafter described) is detachably secured to visor 24. As best shown in FIG. 8, shield 41 in flat condition has a preferably slightly arcuate upper edge 42 and formed immediately below edge 42 are holes 43 spaced the same distance apart as the arcuate distances between studs 39. To facilitate the studs 39 snaping into and out of the holes 43, radial slits 44 are formed in the shield 41 which provide prongs which engage under the studs 39. Thus, the shield 41 may be snapped onto the visor 24 or removed therefrom. Preferably the shield 41 is sufficiently inexpensive so that it may be discarded between uses but, if economy is a factor, the shield may be washed between patients.

Figure 1:
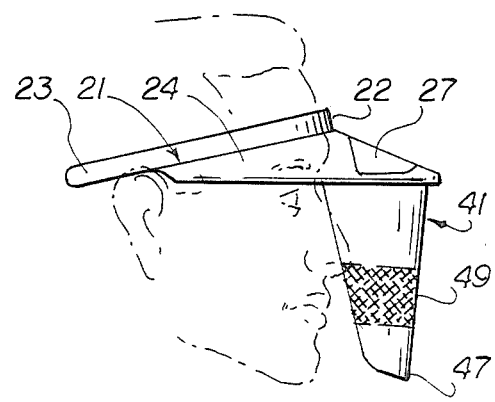
FIG. 1 is a perspective view showing the mask in use.

Although the shape of the shield 41 is subject to some modification, it preferably covers the eyes, nose and mouth of the user so that in transverse horizontal section it is approximately semicircular. Thus, the sides 46 of shield 41 converge, terminating in a bottom edge 47 which, in the form of the invention shown in FIG. 1 is at a level about the chin of the user. Uncontaminated air enters behind the shield 41 and any breath expelled from the mouth is discharged from the atmosphere rather than being rebreathed. This is particularly facilitated when the cover 27 is in open position.

For some uses, particularly in dentistry, a filter 49 of an orange plastic which filters ultraviolet or high wavelength the blue light is disposed across the shield 41 at a level slightly below the nose. In normal use, the filter 49 is out of the line of sight through the shield 41. Dentists frequently use ultraviolet or blue light lamps (not shown) to cure plastic tooth-filling materials. By tilting the head upward and directing the eyes, the filter 49 may be interposed between the instrument emitting the ultraviolet light and the eyes of the wearer to protect against damage. Filter 49 may be of other colors, depending upon conditions under which the mask is used. Preferably, the outer surface of shield 41 in the region of band 49 is silvered to further filter undesired rays.

Figure 7:
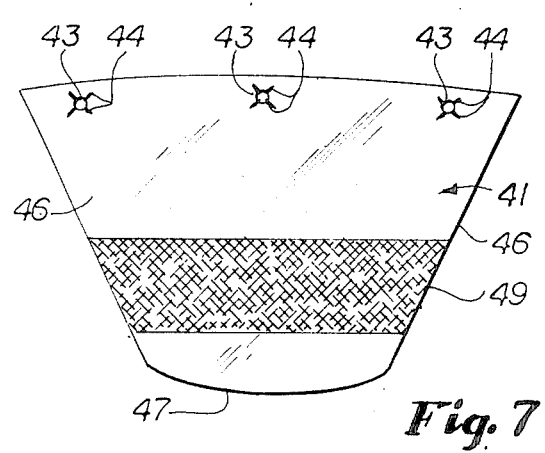
FIG. 7, 8, 9 and 10 are views showing shields which may be used in the present invention in flat condition prior to installation.

As shown in FIG. 8, the filter 49a may be of a different shape than that of FIG. 7. Thus, there is a straight upper edge 51 extending only partially across the width of the shield 41a and the underside edge 52 of band 49a is curved upwardly. The sides 53 are rounded. The mask of FIG. 9 gives improved lateral vision and yet performs the necessary filtering function.

Figure 9:
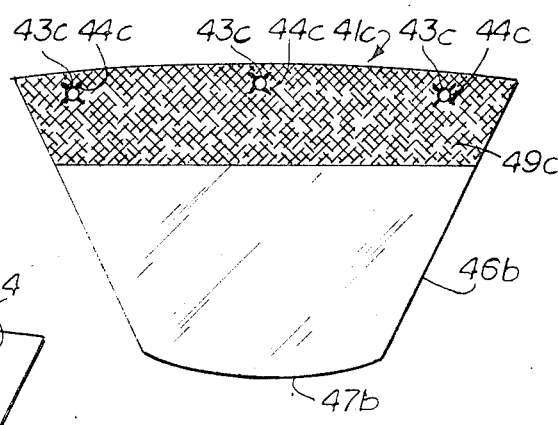

In FIG. 9, the band 49c is located at the extreme upper end shield 41c.

Figure 10:
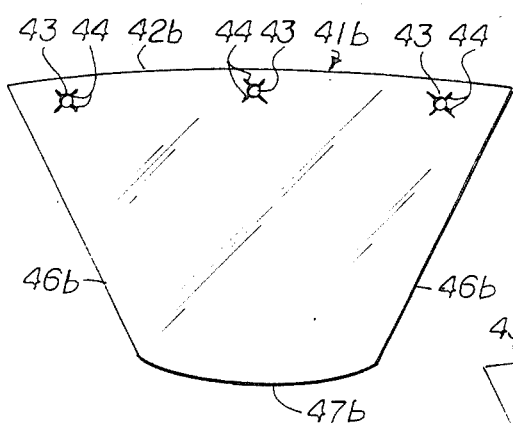

FIG. 10 shows a shield 41b having no filter incorporated therein which may be suitable for users who do not need the protection of a filter by reason of the nature of their work.

In other respects, the shields of FIG. 8, 9 and 10 resemble the preceding embodiment and the same reference numerals followed by subscripts a, c and b, respectively, designate corresponding parts.

Directing attention to the simplification of the invention shown in FIGS. 11–16, the vent 26e in the visor 24d may be left open for ventilation purposes since the possibility of contaminating substances entering through the vent and contaminating the wearer of the mask is minimal. However, as a safety precaution, a modified cover 27d is illustrated. Such a cover has a forward side 56 which is curved in two planes and is provided with vertical ends 57 on either side. Various means may be used to secure the cover 57d in place. In the form shown, particularly in FIGS. 13 and 14, a plurality of hooks 58 are fixed to the bottom edge of side 56 and ends 57 which snap under the margins of the hole 56d. The cover 57 is sufficiently flexible by reason of its thin construction so that the fingers may be used to deform the cover 27d to snap the hooks 58 in place.

To reinforce the visor 24d and also to provide an improved means for attachment of the shield 51d thereto, an arcuate ledge 61 is formed projecting vertically down from the underside of the visor 24d. A center projection 62 and end projections 63 on either side extend from the rear face of the ledge 61. The projections 62, 63 may be of various shapes. In the form of the invention shown in FIG. 15, the projections 63 on either side each has a vertical leg 69 and on either side of leg 69 are truncated round, flat projections 70. Center projection 62 is an inversion of projection 63.

The shield 41d used with projections 62, 63 is formed with a center hole 66 and end holes 67 which are complementary to the projections 62, 63 and are spaced apart a distance equal to the arcuate length between the projections 62 and 63.

Figure 16:
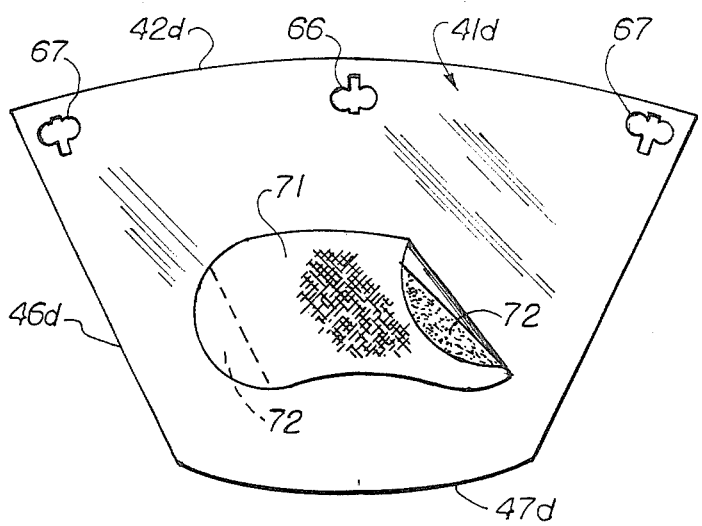
FIG. 16 is an elevational view of a shield used with the modification of FIG. 13 and also showing a modified filter.
Figure 14:
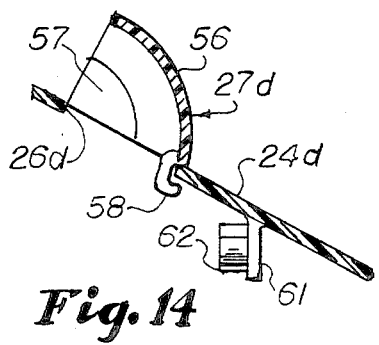
FIG. 14 is a sectional view taken along lines 14—14 of FIG. 13.

FIG. 16 shows a further modification in the use of a filter 71 which is detachable and re-usable. The shape of the filter 71 is subject to variation in that it may be similar to that of filter 49 shown in FIG. 1 or the filters 49a, 49c or any other shape. Filter 71 may be formed in a thin sheet of orange plastic material or other transparent or translucent material which filters out the ultra violet or blue light heretofore mentioned. Along all or a portion of the right and left margins of the filter 71 are bands of pressure sensitive adhesive 72. Adhesive 72 may be used to attach the filter 71 in any position on shield 41d, preferably on the rear face thereof to avoid contaminating spray or splatter.

The filter 71 may be applied in any position where it is most useful to the worker. It may be removed when the shield 41d is being cleaned and then replaced. Further, it will be understood that many users of the mask do not require a filter and, hence, a standard clear shield may be furnished and a supply of filters 71 provided which may be attached to perform the filtering function as desired.

In other respects the structure of FIGS. 11–16 resembles that of the preceding modifications and the same reference numerals followed by the subscript d is to designate corresponding parts.

What is claimed is:

1. A face mask comprising a visor, first means for supporting said visor projecting forward from the head of the wearer above eye level, a shield supported by said visor, said shield being transparent over at least a substantial portion of its area, and second means attaching said shield to said visor to extend down from said visor to below the mouth and around the face to protect the eyes, nose and mouth, said first means comprising a resilient band having a center around the front of the head and discrete, thin, flexible ends engaging the sides of the head, said ends terminating spaced from the back of the head.

2. A mask according to claim 1 in which said visor is formed with an opening.

3. A mask according to claim 2 which further comprises a cover for said opening.

4. A mask according to claim 3 which further comprises hinge means connecting said cover to said visor whereby said cover may be moved between covered and uncovered positions.

5. A mask according to claim 3 in which said cover is removable and which further comprises detachable means securing the cover in said opening.

6. A mask according to claim 4 in which said cover has a protective position extending upward-rearward from the forward edge of said opening.

7. A mask according to claim 1 in which said shield is formed of a sheet of flexible transparent plastic having an upper edge and downward converging side edges.

8. A face mask comprising a visor, first means for supporting said visor projecting forward from the head of the wearer above eye level, a shield, said shield being transparent over at least a substantial portion of its area, and second means attaching said shield to said visor to extend down from said visor to below the mouth and around the face to protect the eyes, nose and mouth, said shield being formed of a sheet of flexible, transparent plastic having an upper edge and downward converging side edges, said filter comprising a piece of filter material and detachable means for attaching a filter, said piece to said sheet of transparent plastic.

9. A face mask comprising a visor, first means for supporting said visor projecting forward from the head of the wearer above eye level, a shield, said shield being transparent over at least a substantial portion of its area, and second means attaching said shield to said visor to extend down from said visor to below the mouth and around the face to protect the eyes, nose and mouth, said shield being provided with a filter area to protect eyes from harmful rays.

10. A mask according to claim 1 in which said second means is detachable whereby said shield may be replaced.

11. A mask according to claim 10 in which said visor is provided with first fastening means and said shield with cooperating second fastening means, one said fastening means being resilient.

12. A mask according to claim 11 in which said first fastening means comprises a plurality of studs fixed to the underside of said visor adjacent the forward edge of said visor and said second fastening means comprises a plurality of holes formed adjacent the upper edge of said shield spaced and shaped to receive said studs.

13. A mask according to claim 12 in which at lease one said stud has an irregular shape.

14. A mask according to claim 12 in which said shield is formed with a plurality of short slits extending outward of said holes to make said shield flexible near said holes.

15. A mask according to claim 12 which further comprises a reinforcing ledge depending from the underside of said visor, said studs being fixed to the rearward face of said ledge.

16. A mask according to claim 9 in which said filter comprises a band of orange pigment across said shield having its upper edge below the level of the eyes.

17. A mask according to claim 16 in which said band terminates on both sides short of the side edges of said shield.

18. A mask according to claim 9 in which said filter comprises a band extending across the top of said shield.

19. A mask according to claim 9 in which said filter is on the inside of said shield and which further comprises a mirror fixed on the outside of said shield.

20. A shield for a mask of the type described comprising a sheet of flexible, transparent plastic having an upper edge and is formed with a plurality of holes spaced slightly below the said upper edge.

21. A shield according to claim 20 formed with a plurality of short slits extending outward from said holes to make said shield flexible near said holes.

22. A shield according to claim 20 in which said shield has downward converging side edges.

23. A shield according to claim 20 in which said shield is provided with a filter area to protect the eyes from harmful rays.

24. A shield according to claim 23 in which said filter comprises a band of orange pigment across said shield having its upper edge below the level of the eyes.

25. A shield according to claim 24 in which said band terminates on both ends short of the side edges of said shield.

26. A shield according to claim 24 in which said filter comprises a band extending across the top of said shield.

27. A shield according to claim 24 which said filter is on the inside of said shield and which further comprises a mirror finish on the outside of said shield.

28. A shield according to claim 23 in which said filter comprises a piece of filter material and detachable means for attaching said piece to said sheet of transparent plastic.

29. A shield according to claim 20 in which at least one said hole is formed with a vertical leg and round cutouts on either side of said leg.

30. A shield according to claim 20 in which a first said hole is formed in the center of said mask and second and third holes are formed on opposite sides of said first hole, each said second and third hole having a vertical leg and round cutouts on either side of said leg.

* * * * *